United States Patent
Druliner et al.

(10) Patent No.: US 6,753,440 B2
(45) Date of Patent: Jun. 22, 2004

(54) COPPER-CATALYZED VAPOR PHASE HYDROCYANATION OF DIOLEFINIC COMPOUNDS

(75) Inventors: Joe Douglas Druliner, Newark, DE (US); Mark Andrew Harmer, Kennett Square, PA (US); Norman Herron, Newark, DE (US); Daniel LeCloux, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/140,736

(22) Filed: May 8, 2002

(65) Prior Publication Data

US 2003/0045740 A1 Mar. 6, 2003

Related U.S. Application Data

(60) Provisional application No. 60/290,294, filed on May 11, 2001.

(51) Int. Cl.[7] .............................................. C07C 253/10
(52) U.S. Cl. ..................................................... 558/335
(58) Field of Search ............................ 558/335; 502/36

(56) References Cited

U.S. PATENT DOCUMENTS

| 2,077,260 | A |  | 4/1937 | Polisso |
| 3,547,972 | A |  | 12/1970 | Drinkard, Jr. |
| 3,574,701 | A |  | 4/1971 | Kominami et al. |
| 3,578,695 | A |  | 5/1971 | Milberger et al. |
| 3,584,029 | A |  | 6/1971 | Kominami et al. |
| 3,766,237 | A |  | 10/1973 | Chia et al. |
| 3,865,863 | A |  | 2/1975 | Field et al. |
| 3,869,500 | A |  | 3/1975 | Kominami et al. |
| 4,230,634 | A |  | 10/1980 | Benzie et al. |
| 4,240,976 | A |  | 12/1980 | Benzie et al. |
| 5,449,807 | A | * | 9/1995 | Druliner ..................... 558/338 |
| 5,916,837 | A |  | 6/1999 | Harmer et al. |

FOREIGN PATENT DOCUMENTS

WO    WO 9616022    5/1996

* cited by examiner

*Primary Examiner*—Joseph K. McKane
*Assistant Examiner*—Ebenezer Sackey

(57) ABSTRACT

A catalyzed vapor phase process for the hydrocyanation of acyclic diolefinic compounds to olefinic nitriles is described in which the olefinic double bond is not conjugated to the triple bond of the cyano group, wherein a catalyst composition comprising supported copper salts is used.

18 Claims, No Drawings

COPPER-CATALYZED VAPOR PHASE HYDROCYANATION OF DIOLEFINIC COMPOUNDS

This application claims the benefit of U.S. Provisional Application No. 60/290,294, filed May 11, 2001, which is incorporated in its entirety as a part hereof.

FIELD OF INVENTION

This invention generally relates to a gas phase process for the hydrocyanation of diolefinic compounds to produce nonconjugated acyclic nitriles. In particular, the invention relates to a gas phase process for the hydrocyanation of diolefinic compounds to produce nonconjugated acyclic nitriles utilizing catalyst compositions comprising copper salts, dispersed on supports, including carbon, silica, alumina and a variety of metal oxides.

BACKGROUND

Catalytic hydrocyanation systems, particularly pertaining to the hydrocyanation of olefins, are known in the art. For example, liquid phase systems useful for the hydrocyanation of butadiene to form pentenenitriles (PNs) are known in the art, e.g., U.S. Pat. No. 3,766,237. As used in that patent and as will be used herein, the term "pentenenitrile" is intended to mean a cyanobutene. Likewise, "butenenitrile" means cyanopropene. The pentenenitriles so formed are further subjected to hydrocyanation and, in some cases isomerization, to form adiponitrile (ADN), a commercially important material in the manufacture of nylon.

The overwhelming majority of prior art processes for the hydrocyanation of butadiene are conducted in the liquid phase, with all attendant waste disposal problems. For example, U.S. Pat. No. 4,240,976 utilized copper halide as a catalyst; U.S. Pat. No. 4,230,634 utilized copper inorganic salts in the presence of organic nitriles; and U.K. Patent No. 2,077,260 used copper bonded to a peroxo group. Previous approaches toward carrying out gas phase hydrocyanation of olefinic compounds have usually started with monoolefinic, not diolefinic, compounds and have given rise primarily to saturated products, which could not be further hydrocyanated. For example, U.S. Pat. No. 3,584,029 teaches that propionitrile is prepared by reaction of HCN with ethylene over catalysts containing Ni salts, $H_3PO_4$ and $Al_2O_3$; and U.S. Pat. No. 3,547,972 discloses the reaction of HCN and butadiene in the gas phase over a mixed metal catalyst containing copper chromite and activated copper chromite, which does yield a mixture of pentenenitriles, with 77–82% selectivities to 3-pentenenitrile and 4-pentenenitrile. However, the reaction of U.S. Pat. No. 3,547,972 also requires a co-feed of HCl.

Several patents teach that reaction of HCN with butadiene, ethylene, propylene or butenes, and additionally with air or oxygen in the gas phase, over various supported metal-containing catalysts give rise to cyanated olefinic products. However, in the olefinic products so produced the olefinic double bond is usually conjugated with the triple bond of the cyano group, and, therefore, substantially useless for the production of adiponitrile. For example, see:

U.S. Pat. No. 3,865,863, Asahi, Feb. 11, 1975

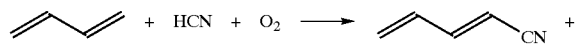

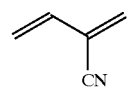

U.S. Pat. No. 3,574,701, Asahi K.K.K., Apr. 13, 1971

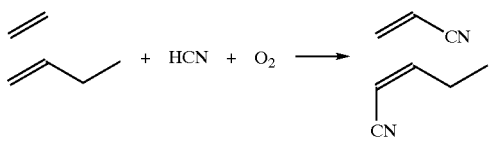

U.S. Pat. No. 3,578,695, Standard Oil, May 11, 1975

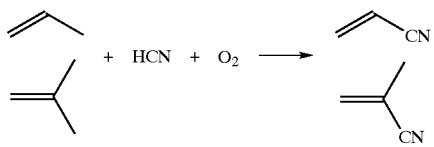

U.S. Pat. No. 3,869,500, Asahi, Mar. 4, 1975

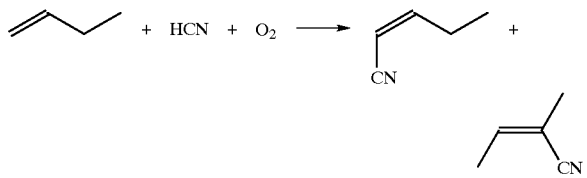

The present invention provides a catalyzed gas phase process for the hydrocyanation of diolefinic compounds which is rapid, selective, and efficient. While certain solvents or diluents can be used in this process, they can be eliminated altogether. Furthermore, the catalyst composition is utilized as a stationary solid phase, which can reduce the cost of catalyst synthesis, recovery, and recycle, as well as the disposal cost of by-product waste. A corollary benefit is the reduction of the cost of capital equipment needed for the process.

SUMMARY OF THE INVENTION

One embodiment of the invention is a process for the gas-phase hydrocyanation of diolefinic compounds comprising reacting an acyclic, aliphatic, conjugated diolefinic compound with HCN in the gas phase within a temperature range of 135° C. to 200° C. in the presence of a catalyst composition that is a supported copper (I) or (II) fluorinated alkylsulfonate complex. Preferably the support used in such a catalyst composition is selected from the group consisting of silica, alumina, and carbon; more preferably the support is silica or carbon. Preferably the fluorinated alkylsulfonate in the copper complex in the catalyst composition is trifluoromethylsulfonate.

Another embodiment of the invention is a process for the gas-phase hydrocyanation of diolefinic compounds comprising reacting an acyclic, aliphatic, conjugated diolefinic compound with HCN in the gas phase within a temperature range of 135° C. to 200° C. in the presence of a catalyst composition that is a copper (I) or (II) complex supported on a fluorosulfonated support. Also preferably the fluorosulfonated support is a composite of a porous silica network within and throughout which is dispersed either a Nafion® perfluorinated polymer or fluorosulfonic acid.

The process in either case is preferably carried out at a temperature of 155–175° C. The starting diolefinic compound is preferably a diolefin represented by the formula $R^1CH{=}CH{-}CH{=}CHR^2$ wherein each one of $R^1$ and $R^2$, independently, is H or a $C_1$ to $C_3$ alkyl. More preferably the starting diolefinic compound is 1-3-butadiene.

A further embodiment of the invention involves the introduction of HCN and 1,3-butadiene into the reaction without a solvent or diluent. Yet a further embodiment involves dissolving at least one of HCN and 1,3-butadiene in a solvent, inert to the starting materials and to the catalyst composition under the reaction conditions, prior to being introduced into the reaction, with the solution being vaporized prior to its entry into the reaction.

DETAILED DESCRIPTION OF THE INVENTION

A catalyst composition useful in the practice of the present invention includes a copper (I) or (II) fluorinated alkylsulfonate complex supported on a carrier that is neutral and has a low surface area. A complex is one or more metal cations together with its associated anions. A preferred support is silica, alumina, carbon and the like. Commonly used techniques for treatment of supports with metal catalysts can be found in B. C. Gates, *Heterogeneous Catalysis*, Vol. 2, pp. 1–29, Ed. B. L. Shapiro, Texas A & M University Press, College Station, Tex., 1984. Typically, in accordance with this invention, the copper (I) or (II) fluorinated alkylsulfonate complex is dispersed on a silica, alumina or carbon support at a concentration sufficient to produce a catalyst composition, including the support, containing 0.3% wt. to 1.0% wt. copper by weight of the total of the composition.

Fluorinated alkylsulfonates useful in forming a complex with copper include anions or dianions of the structure $R{-}SO_3^-$ or $R{-}(SO_3^-)_2$, where R is a linear or branched polyfluoroalkyl or a perfluoroalkyl group of up to 12 carbon atoms. Preferably R is trifluoromethyl. Anions of the type $(R{-}SO_3)_2N^-$ or $F{-}SO_3^-$ may also be used in place of alkylsulfonates. Nitrile ligands may also be complexed to copper.

Catalyst compositions useful in the practice of the present invention also include copper (I) or (II) complexes supported on a fluorosulfonated support. A fluorosulfonated support contains $R{-}SO_3^-$ groups, where R is as defined above or is $-C_nF_{2n}-$. Preferably the fluorosulfonated support is a composite of a porous silica network within and throughout which is dispersed either a Nafion® perfluorinated polymer or fluorosulfonic acid. Such a composite is more particularly described in U.S. Pat. Nos. 5,824,622, 5,916,837 and 5,948,946.

In the process of the invention, the catalyst composition is loaded into a tubular reactor, and a gaseous diolefinic compound, e.g., butadiene, and HCN are passed continuously over the solid catalyst composition at a temperature sufficiently high to maintain the starting materials as well as the reaction products in the gas phase. The preferred temperature range is from about 135° C. to about 200° C., most preferably from about 155° C. to about 175° C. The temperature must be high enough to maintain all of the reactants and products in the gas phase but low enough to prevent deterioration of the catalyst composition. The particular preferred temperature depends to some extent on the catalyst composition being used, the diolefinic compound being used, and the desired reaction rate. The operating pressure is not particularly critical and can conveniently be from about 1–10 atmospheres (about 101.3 to about 1013 kPa). No practical benefit is obtained when operating above the upper limit of this pressure range.

HCN and/or diolefinic compound starting materials can be delivered as a neat vapor or as a preheated solution in a solvent, such as acetonitrile or toluene. Under atmospheric pressure, using nitrogen or another inert gas as a carrier, a temperature of from about 160° C. to 175° C. is typically used. Nitrogen is preferred because of its low cost. Gaseous oxygen, water vapor, or any other gaseous substance which could react with the HCN, the copper portion of the catalyst composition, or the starting diolefinic compound should be avoided. The reaction products are liquid at room temperature and are conveniently recovered by cooling. Branched 2-methyl-3-butenenitrile can be separated from linear 3-pentenenitrile and 4-pentenenitrile by distillation.

The diolefinic compound reactants used in this invention include primarily conjugated diolefins containing from 4 to 10 carbon atoms; for example 1,3-butadiene and cis and trans-2,4-hexadienes. Butadiene is especially preferred by reason of its commercial importance in the production of adiponitrile. Other suitable diolefinic compounds include diolefinic compounds substituted with groups which do not deactivate the catalyst composition, for example, cis and trans-1,3-pentadienes.

The following Formulas III and IV illustrate suitable representative starting diolefinic compounds; and Formulas V, VI, and VII represent the products obtained from 1,3-butadiene and HCN.

  III

  IV wherein each one of $R^1$ and $R^2$, independently, is H or a $C_1$ to $C_3$ alkyl

  V

  VI

  VII

In the practice of the hydrocyanation process of the present invention, a reactor, such as a tubular reactor, is charged in an inert atmosphere with the desired catalyst composition. The reactor feed and exit lines are preferably purged with an inert gas, such as nitrogen, argon or helium. The reactor is then heated to the desired temperature, either under a continuous flow of inert gas or sealed from the ambient atmosphere. The reactor is fed with the desired diolefinic compound and HCN. These may be fed together or separately, either neat or as solutions in suitable solvents, such as acetonitrile or toluene. The hydrocyanation reaction is, however, preferably carried out without a solvent. If any solvent is used, the solvent should be gaseous at the reaction temperature and pressure and inert towards the diolefinic compound, HCN, and the catalyst. Such solvents include hydrocarbons such as hexane, benzene, or toluene, or nitriles such as acetonitrile. When the reactants are fed continuously, an inert gas carrier normally is employed as well.

The diolefinic compound, HCN and any solvent are passed through a heated portion of feed line heated to the reaction temperature to ensure complete vaporization. The gaseous product mixture exiting the reactor can be passed, if desired, through a heated gas sampling loop of a gas chromatograph for periodically monitoring the progress of the reaction. Alternatively, the gaseous effluent can be cooled to about 0° C. to 25° C. in order to condense all products to liquids. The flow rate of the diolefinic compound preferably is such that its mole ratio to catalyst, per hour of continuous feed, is about 2:1 to 10:1. The mole ratio of the diolefinic compound to HCN normally is at least about 1:1.

The advantageous effects of this invention are demonstrated by a series of examples, as described below. The embodiments of the invention on which the examples are based are illustrative only, and do not limit the scope of the invention. The significance of the examples is better understood by comparing these embodiments of the invention with certain controlled formulations, which do not possess the distinguishing features of this invention. The following abbreviated references are used herein.

| | |
|---|---|
| BD | Butadiene |
| 2M3BN | 2-methyl-3-butenenitrile |
| 3-PN | 3-pentenenitrile |
| 4-PN | 4-pentenenitrile |
| AN | acetonitrile |
| OTf | $CF_3SO_3-$ |
| PNs | Pentenenitriles |

Preparation of Catalyst Compositions

Composition 1

Copper(I) trifluoromethanesulfonate on Sibunit carbon 7

Inside a nitrogen filled glove box, 0.38 g (1 meq) copper (I) (acetonitrile)$_4$—trifluoromethanesulfonate (prepared according to: Kubas, G. J. Inorg. Synth. 1990, 28, 68–70) was dissolved into 5 mL dry acetonitrile. 1.0 g of 12–20 mesh size Sibunit carbon 7 (Boreskov Inst. of Catalysis, Novosibirsk, Russia), dried previously at 850° C. for 5 hrs in dry helium, was added to the solution and then the slurry was stirred for 15 mins. The solvent was evaporated under vacuum and the resulting solid was re-wetted with minimal acetonitrile and re-evaporated to help insure complete incorporation of the copper material into the carbon. The recovered catalyst composition was stored under nitrogen until it was loaded into the hydrocyanation reactor for testing.

Composition 2

Copper(II) trifluoromethanesulfonate on Sibunit carbon 7

The procedure to prepare Composition 1 was repeated exactly except substituting 0.37 g (1 meq) of the copper(II) trifluoromethanesulfonate (Aldrich) for the copper(I) salt.

Composition 3

Copper(I) trifluoromethanesulfonate on EM carbon

The procedure to prepare Composition 1 was repeated except substituting 1 g of dry (850° C. in helium for 5 hrs) 20–40 mesh carbon CX0648-1 from EM Science (480 S. Democrat Rd, Gibbstown, N.J. 08027) for the Sibunit 7 carbon.

Composition 4

Copper(I) trifluoromethanesulfonate on silica

The procedure of example 1 was repeated except substituting 1 g of dry (500° C. in dry air for 1 hr) 10–20 mesh large pore silica-gel granules #89346 from Alfa Aesar (30 Bond Street, Ward Hill, Mass. 01835-8099) for the Sibunit 7 carbon.

Composition 5

Copper(I) trifluoromethanesulfonate on silica modified with Nafion® perfluoronated polymer The procedure to prepare Composition 1 was repeated except substituting for the Sibunit 7 carbon 1 g of dry SAC13 silica coated with Nafion® fluoropolymer (obtained from DuPont and prepared according to a method described in Harmer et al, Chem. Comm., page 1803, 1997).

Composition 6

Copper(I) trifluoromethanesulfonate on fluorosulfonic acid derivatized silica

The procedure to prepare Composition 1 was repeated except substituting 1 g of silica derivatized with fluorosulfonic acid silane groups, containing about 0.2 meq fluorosulfonic acid groups per gram of silica (DuPont) for the Sibunit 7 carbon.

Composition 7

Copper(I) tosylate on EM carbon

The procedure to prepare Composition 3 was repeated except substituting 0.32 g copper(I) (acetonitrile)$_4$ tosylate (prepared according to: Kroneck, P, et al., Z. Naturforsch., A 1982, 37A, 186–190) for the trifluoromethane sulfonate salt.

Composition 8

Copper(I) hexafluoroantimonate on EM carbon

The procedure to prepare Composition 3 was repeated except substituting 0.25 g copper(I) (acetonitrile)$_4$ hexafluoroantimonate (prepared according to: Kubas, op. cit.) for the trifluoromethane sulfonate salt. The final catalyst was dried in flowing helium at 150° C. for 1 hr then stored under nitrogen.

Composition 9

Copper(I) hexafluorophosphate on EM carbon

The procedure to prepare Composition 3 was repeated except substituting 0.25 g copper(I) (acetonitrile)$_4$ hexafluorophosphate (prepared according to: Kubas, op. cit.) for the trifluoromethane sulfonate salt. The final catalyst composition was dried in flowing helium at 150° C. for 1 hr then stored under nitrogen.

Composition 10

Copper(I) chloride on EM carbon

The procedure to prepare Composition 3 was repeated except substituting 0.12 g copper(I) chloride (Aldrich) for the trifluoromethane sulfonate salt.

Composition 11

Copper metal on EM carbon 1 g of dry (850° C. helium for 5 hrs) EM carbon as described above was slurried into a solution of 0.25 g copper(II) nitrate hydrate dissolved in methanol. The slurry was stirred then evaporated to dryness. The impregnated carbon was then calcined in flowing helium at 300° C. for 1 hr and then cooled to 200° C. The gas flow was switched to hydrogen and held at 200° C. for 1 hr. The material was flushed with nitrogen and cooled and then stored under nitrogen until testing.

Composition 12

Copper(I) exchanged zeolite Y 2 g of zeolite NaY (LZY–52 from Aldrich) was dried at 500° C. in flowing air for 4 hrs. This material was slurried into a solution of 1.0 g copper(I) (acetonitrile)4 trifluoromethanesulfonate in 25 mL dry acetonitrile in a nitrogen filled glove box and stirred for 16 hrs. The solid was filtered off and washed with acetonitrile before drying in flowing nitrogen at 200° C. for 2 hrs. The copper(I) exchanged zeolite catalyst was stored under nitrogen until testing.

EXAMPLES 1–6

Gas-Phase Hydrocyanation of Butadiene

An empty 0.25-inch (0.64 cm) diameter, 15-inch (37.5 cm) long stainless steel tubular reactor was placed in a nitrogen-filled glove box. A plug of glass wool was placed in the bottom end of the reactor, followed by the amount and type of catalyst composition shown in Table 1. A thermocouple was inserted into the top of the reactor. Both ends of the reactor were sealed with metal fittings, and the reactor was removed from the glove box and connected to stainless steel reactor feed lines purged with nitrogen. Attached to the outlet side of the reactor was a valve which could be switched to either a waste receiver or a heated tubing line for diverting the gaseous effluent to an injector for analysis by gas chromatography (GC). GC analyses were done on a 30 m DB-23 capillary column of a 0.32 mm integral diameter, supplied by J&W Scientific, Folsom, Calif. The stationary phase was cyanopropyl (50%) methylpolysiloxane. Feed streams consisted of nitrogen, gaseous butadiene and, typically, an acetonitrile solution containing HCN and also including cyclohexane as an internal GC standard. The combined feed streams were preheated to 150° C. to ensure complete vaporization. The reactor was heated in a split tube furnace to the temperatures shown in Table 1. Product samples were collected, generally every hour. Table 1 shows the specific reaction conditions and summarizes the results.

Controls A~F

Gas-Phase Hydrocyanation of Butadiene

Controls A~F show comparative versions of the hydrocyanation of butadiene using several Cu(I) salts dispersed on carbon which are either inactive or exhibit short-lived low activity. Controls A~F were run under a process comparable to that of Examples 1~6. Control E shows complete inactivity for Cu(0) dispersed on carbon, and Control F shows that $Cu(AN)_4OTf$ ion-exchanged into zeolite Y is nearly inactive, compared to high activity when dispersed on Sibunit carbon (Table 1, Example 1). Table 2 shows the specific reaction conditions and summarizes the results.

Percent conversion of HCN was calculated as (measured GC area % for PNs/measured GC area % for cyclohexane)× (GC response factor for PNs)×(mmoles of cyclohexane fed per hour/mmoles of HCN fed per hour)×100. Response factor is the number, characteristic for each compound, required for converting area percent to mole percent of PNs. Percent Linear was determined as 100 times the ratio of GC area % (3PN+4PN)/GC area % (3PN+4PN+2M3BN). Percent selectivity to useful PNs (3PN+4PN+2M3BN) was determined as 100 times the ratio of GC area % (3PN+4PN+ 2M3BN)/GC area % (all PNs).

TABLE 1

Gas-Phase Hydrocyanation of Butadiene, Examples 1–6

| Example | Catalyst Composition (Support) | Catalyst Comp., g (Cu, m eq.) | Feed rate, m mole/hr BD | Feed rate, m mole/hr HCN | $N_2$, cc/min | Temp., ° C. | Elapsed time, hr | % Linear | % HCN Conv. | % Select. Useful PNs |
|---|---|---|---|---|---|---|---|---|---|---|
| 1 | $Cu(AN)_4OTf$ (Sibunit Carbon) | 1.03 (1.0) | 2.1 | 1.1 | 5 | 175 | 1.1 | 88.9 | 56.2 | 100 |
|  |  |  |  |  |  |  | 3.2 | 88.2 | 81.6 | " |
|  |  |  |  |  |  |  | 5.2 | 91.1 | 99.5 | " |
|  |  |  |  |  |  |  | 7.2 | 92.8 | 78.4 | " |
|  |  |  |  |  |  |  | 9.3 | 91.9 | 64.5 | " |
|  |  |  |  |  |  |  | 11.3 | 89.2 | 54.1 | " |
|  |  |  |  |  |  |  | 13.3 | 90.0 | 51.4 | " |
|  |  |  |  |  |  |  | 15.4 | 91.7 | 39.5 | " |
| 2 | $Cu(OTf)_2$ (Sibunit Carbon) | 1.6 (1.0) | 2.1 | 1.1 | 5 | 175 | 2 | 84.2 | 48.5 | 100 |
|  |  |  |  |  |  |  | 3 | 84.0 | 40.9 | " |
|  |  |  |  |  |  |  | 5 | 86.7 | 49.8 | " |
|  |  |  |  |  |  |  | 7 | 91.2 | 69.7 | " |
|  |  |  |  |  |  |  | 9.1 | 90.8 | 89.6 | " |
|  |  |  |  |  |  |  | 11.1 | 90.5 | 81.7 | " |
|  |  |  |  |  |  |  | 13.1 | 90.9 | 66.5 | " |
|  |  |  |  |  |  |  | 15.1 | 89.0 | 58.5 | " |
| 3 | $Cu(AN)_4OTf$ (EM Carbon) | 1.48 (1.0) | 4.0 | 2.9 | 0 | 160 | 1.5 | 88.2 | 24.5 | 100 |
|  |  |  |  |  |  |  | 2.8 | 90.3 | 33.3 | " |
|  |  |  |  |  |  |  | 3.8 | 90.0 | 20.1 | " |
|  |  |  |  |  |  |  | 4.8 | 90.0 | 11.6 | " |
|  |  |  |  |  |  |  | 22.3 |  | 0.9 | " |
| 4 | $Cu(AN)_4OTf$ (Silica) | 1.33 (1.0) | 2.1 | 1.2 | 5 | 175 | 1 | 88.5 | 41.4 | 100 |
|  |  |  |  |  |  |  | 2.5 | 88.8 | 83.9 | " |
|  |  |  |  |  |  |  | 6.5 | 89.0 | 65.8 | " |

TABLE 1-continued

Gas-Phase Hydrocyanation of Butadiene, Examples 1–6

| Example | Catalyst Composition (Support) | Catalyst Comp., g (Cu, m eq.) | Feed rate, m mole/hr BD | HCN | N₂, cc/min | Temp., °C. | Elapsed time, hr | % Linear | % HCN Conv. | % Select. Useful PNs |
|---|---|---|---|---|---|---|---|---|---|---|
| | | | | | | | 12.5 | 87.9 | 50.0 | " |
| | | | | | | | 17.5 | 88.8 | 38.1 | " |
| | | | | | | | 21.5 | 93.2 | 33.4 | " |
| 5 | Cu(AN)₄OTf (Nafion ®/Silica) | 1.19 (1.0) | 2.1 | 1.2 | 5 | 175 | 1 | 87.8 | 78.9 | 100 |
| | | | | | | | 2.5 | 90.2 | 97.1 | " |
| | | | | | | | 5.1 | 90.1 | 88.8 | " |
| | | | | | | | 9.1 | 87.1 | 96.5 | " |
| | | | | | | | 16.1 | 90.2 | 72.6 | " |
| | | | | | | | 20.1 | 89.2 | 52.7 | " |
| | | | | | | | 24.5 | 89.3 | 34.1 | " |
| 6 | Cu(AN)₄OTf (derivatized Silica) | 1.63 [ ] | 2.1 | 1.2 | 5 | 175 | 0.5 | 45.5 | 14 | 100 |
| | | | | | | | 3.5 | 86.2 | 105.4 | " |
| | | | | | | | 6.5 | 91.5 | 98.7 | " |
| | | | | | | | 12.5 | 90.6 | 88.9 | " |
| | | | | | | | 19.5 | 90.3 | 78.4 | " |
| | | | | | | | 24.5 | 88.4 | 56.3 | " |

TABLE 2

Gas-Phase Hydrocyanation of Butadiene, Controls A–F

| Example | Catalyst Composition (Support) | Catalyst Comp., g (Cu, m eq.) | Feed rate, milli mole/hr BD | HCN | N₂, cc/min | Temp., °C. | Elapsed time, hr | % Linear | % HCN Conv. | % Select. Useful PNs |
|---|---|---|---|---|---|---|---|---|---|---|
| A | Cu(tosylate) (EM Carbon) | 1.36 (1.0) | 4.0 | 2.9 | 0 | 160 | 1 | | 2.0 | 100 |
| | | | | | | | 2 | | 3.3 | " |
| | | | | | | | 4 | | 1.4 | " |
| | | | | | | | 5 | | 1.0 | " |
| B | Cu(AN)₄SbF₆ (EM Carbon) | 0.62 [0.27] | 5.4 " " | 2.6 1.3 " | " " " | 165 " 185 | 1 3 5.6 | | trace " 0 | |
| C | Cu(AN)₄PF₆ (EM Carbon) | 0.5 [0.27] | 5.4 | 1.0 | " | 165 | 1 3 5 | | 0 " " | |
| D | CuCl (EM Carbon) | 1.14 (1.0) | 4.0 | 2.9 | " | 160 " 180 " | 2.2 3.3 5.1 6.2 | | 1.8 1.3 0.6 0.3 | |
| E | Cu(O) (EM Carbon) | 0.58 [0.71] | 5.4 | 2.6 | " | 165 185 100 | 3.5 5.8 8.8 | | 0 " " | |
| F | Cu(AN)₄OTf (Zeolite Y) | 1.05 [0.9] | 4.0 | 2.5 | " | 165 | 1.1 2.2 | | trace 0 | |

In Examples 1~6, the percent conversion of HCN is in general much higher than in Controls A~F.

What is claimed is:

1. A process for the gas-phase hydrocyanation of diolefinic compounds, comprising reacting an acyclic, aliphatic, conjugated diolefinic compound with HCN in the gas phase in the presence of a catalyst composition comprising either:
   (a) a supported copper (I) or (II) fluorinated alkylsulfonate complex; or
   (b) a copper (I) or (II) complex supported on a fluorosulfonated support.

2. The process of claim 1 wherein the support in Composition (a) is selected from the group consisting of silica, alumina, and carbon.

3. The process of claim 2 wherein the support is silica or carbon.

4. The process of claim 1 wherein the reaction is carried out at a temperature of about 135 to about 200° C.

5. The process of claim 1 wherein the starting diolefinic compound is a diolefin represented by the formula

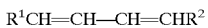

$$R^1CH=CH—CH=CHR^2$$

wherein each one of $R^1$ and $R^2$, independently, is H or a $C_1$ to $C_3$ alkyl.

6. The process of claim 5 wherein the diolefinic compound is 1-3-butadiene.

7. The process of claim 1 wherein the diolefinic compound is substituted with at least one other group which does not deactivate the catalyst composition.

8. The process of claim 7 wherein HCN and 1,3-butadiene are introduced into the reaction without a solvent or diluent.

9. The process of claim 7 wherein at least one of HCN and 1,3-butadiene is dissolved in a solvent, inert to the starting materials and to the catalyst composition under the reaction conditions, prior to being introduced into the reaction, but the solution is vaporized prior to its entry into the reaction.

10. The process of claim 1 which is a continuous process.

11. The process of claim 1 which is a batch process.

12. The process of claim 11 wherein the flow rate of the diolefinic compound is such that its mole ratio to the catalyst composition, per hour of continuous feed, is between about 5:1 and about 100:1.

13. The process of claim 1 wherein the mole ratio of diolefinic compound to HCN is at least about 1:1.

14. The process of claim 1 which is conducted at a pressure within the range of about 101.3 to about 1013 kPa.

15. The process of claim 1 wherein the catalyst composition comprises Composition (a), a supported copper (I) or (II) fluorinated alkylsulfonate complex.

16. The process of claim 15 wherein the fluorinated alkylsulfonate is trifluoromethylsulfonate.

17. The process of claim 1 wherein the catalyst composition comprises Composition (b), a copper (I) or (II) complex supported on a fluorosulfonated support.

18. The process of claim 17 wherein the fluorosulfonated support is a composite of a porous silica network within and throughout which is dispersed either a perfluorinated polymer or fluorosulfonic acid.

* * * * *